United States Patent [19]

Vecere et al.

[11] Patent Number: 5,522,272

[45] Date of Patent: Jun. 4, 1996

[54] GAS EMISSION SAMPLE CONTAINER WITH HEATING MEANS

[75] Inventors: William T. Vecere, Warren; James M. Suddath, West Bloomfield, both of Mich.

[73] Assignee: Bellaire Industries, Inc., Royal Oak, Mich.

[21] Appl. No.: 443,090

[22] Filed: May 17, 1995

Related U.S. Application Data

[63] Continuation of Ser. No. 152,201, Nov. 4, 1993, abandoned.

[51] Int. Cl.⁶ .................................................. G01N 1/00
[52] U.S. Cl. ................................. 73/864.62; 73/863.11
[58] Field of Search .......................... 73/863.11, 864.91, 73/864.33–864.35, 864.51, 864.62, 864.63, 23.31–23.33, 863.62; 219/201, 385, 438, 439, 442; 383/127

[56] References Cited

U.S. PATENT DOCUMENTS

| | | |
|---|---|---|
| 3,332,415 | 7/1967 | Ericson . |
| 3,357,632 | 12/1967 | Stanforth . |
| 3,603,155 | 9/1971 | Morris et al. . |
| 3,759,667 | 9/1973 | Bannister et al. . |
| 3,793,887 | 2/1974 | Anderson et al. ............. 73/863.11 |
| 3,869,842 | 3/1975 | Verbeke ............................ 53/14 |
| 3,977,708 | 8/1976 | Jopp . |
| 4,546,659 | 10/1985 | Gill et al. . |
| 4,548,321 | 10/1985 | Möckesch et al. . |
| 4,587,402 | 5/1986 | Nishino et al. ................. 392/438 |
| 4,700,531 | 10/1987 | Hsu et al. . |
| 4,718,778 | 1/1988 | Ichikawa . |
| 4,772,134 | 9/1988 | Jensen et al. . |
| 4,817,423 | 4/1989 | Christiansen . |
| 4,893,731 | 1/1990 | Richter . |
| 4,998,990 | 3/1991 | Richter et al. . |
| 5,074,155 | 12/1991 | Vecere . |
| 5,218,874 | 6/1993 | Vecere . |
| 5,239,877 | 8/1993 | Suddath et al. . |

FOREIGN PATENT DOCUMENTS

| | | |
|---|---|---|
| 1249717 | 9/1967 | Germany . |
| 4-71186 | 3/1992 | Japan ................................. 392/438 |

Primary Examiner—Robert Raevis
Attorney, Agent, or Firm—Young and Basile

[57] ABSTRACT

The temperature of gas stored within a gas emission sample container is maintained at a predetermined, constant temperature. In one embodiment, a heater is mounted in a receptacle formed on and adjacent to one of the side walls of the container. The heater is in the form of a planar arranged electric coil. A reflective surface is mounted in the receptacle next to one surface of the heater for reflecting heat from the heater toward the adjacent side wall of the container. The side wall of the container adjacent the heater is preferably of a black material for enhanced heat absorption. In another embodiment, at least one of the side walls of the container is formed of a black material for enhanced heat absorption. A heater is disposed in proximity with the container for generating heat which is absorbed by the black side wall of the container.

9 Claims, 1 Drawing Sheet

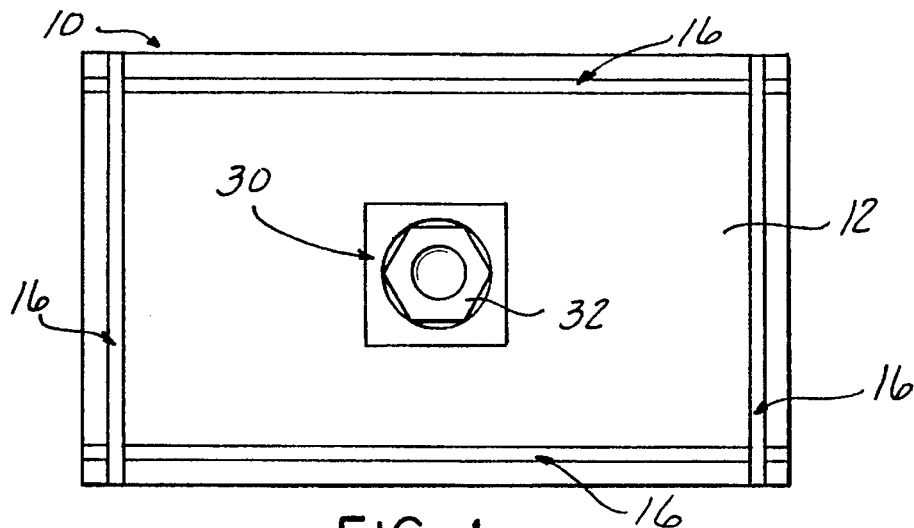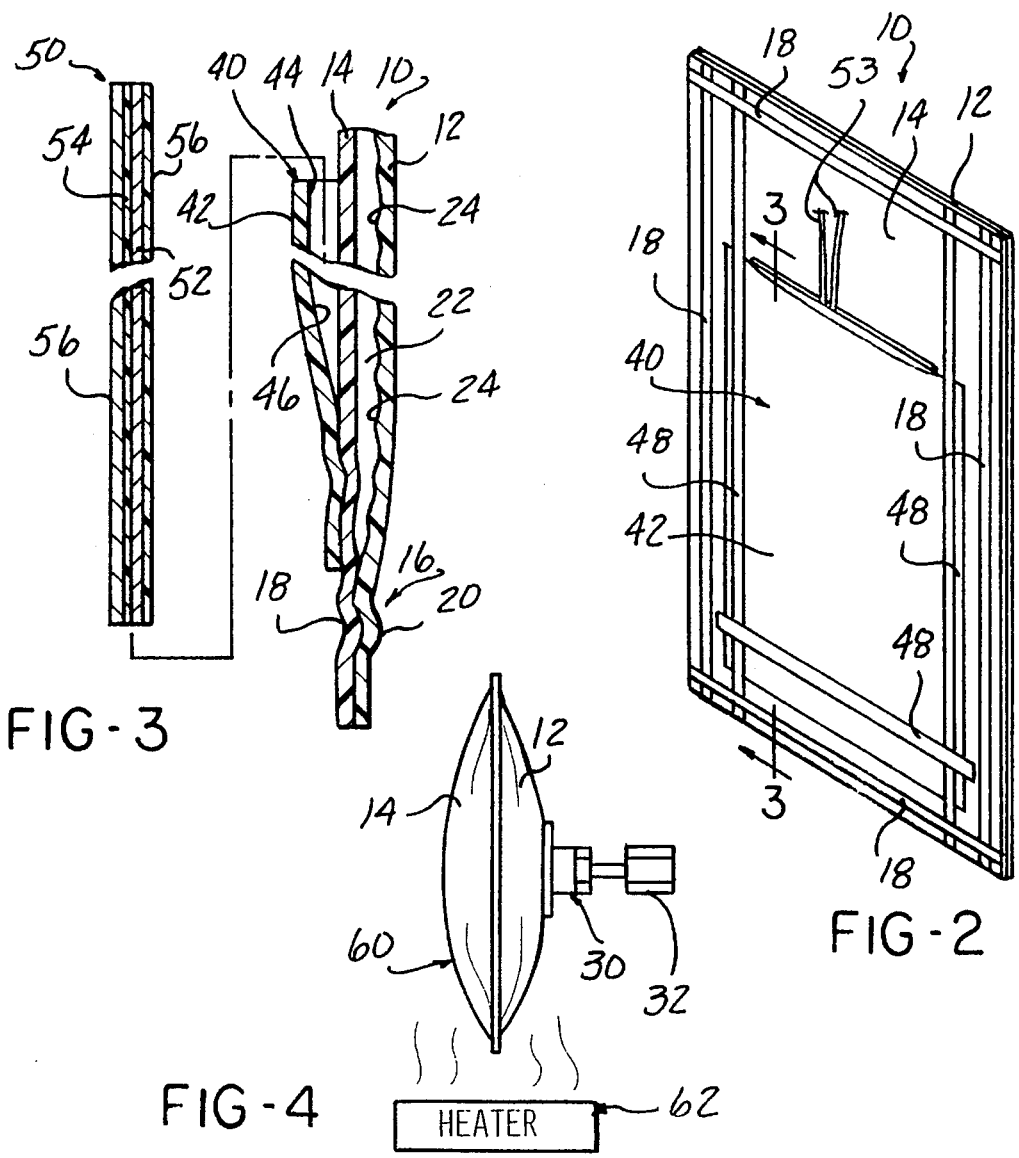

GAS EMISSION SAMPLE CONTAINER WITH HEATING MEANS

This application is a CONTINUATION of application Ser. No. 08/152,201, filed on Nov. 4, 1993, now abandoned.

BACKGROUND OF THE INVENTION

1. Field of the Invention

The present invention relates to gas emission sample containers for collecting gas emissions from motor vehicles.

2. State of the Art

Expandable, sealed containers or bags are employed for collecting and temporarily storing gas emissions from motor vehicles before the collected emissions are analyzed by suitable test equipment. Such containers are expandable to a predetermined volume to collect a known quantity of gaseous emissions.

Typically, a plurality of such containers, such as six containers, are connected through suitable conduits, valves, etc., to a test apparatus to collect separate quantities of gas emissions from a vehicle and from ambient atmosphere. The emission samples from a motor vehicle under test are collected in the sealed containers as the motor vehicle is operated according to a prescribed test schedule corresponding to various engine operating conditions.

The expandable containers include a fitting sealingly mounted in each container which is connected to the test apparatus to receive gas emissions from the vehicle under test. The fitting directs the gas emissions into the container for storage, as well as enabling the stored gas contents to be evacuated from the container for subsequent analysis. The fitting and the sealed container are made of a chemically inert material, such as a fluorinated carbon plastic, i.e., plastics sold under the registered trademarks TEFLON, KYNAR, and/or TEDLAR.

Accurate testing of gasses in a gas emission sample container requires the complete inflation of the container to a constant volume without internal dead spots as well as the complete evacuation of all gasses from the container. Specially designed, small, smooth fitting have been employed in gas emission sample containers to prevent the formation of internal dead spots during the evacuation of gas from such containers. In addition, hollow conduits or tubes having spaced apertures formed therein have been mounted within such containers and connected to the fitting to ensure complete and even inflation and evacuation of gas to and from the container, without stratification of the gas within the container.

It is also known to maintain the pressure of the gas emission sample container, when inflated to a known volume, at a constant pressure during storage and subsequent evacuation of gas therefrom. This prevents any change in volume of the gas due to pressure variations. However, the temperature of the gas may vary considerably due to the length of time between the storage of the gas in the container and its subsequent evacuation for testing as well as the length of the conduits between the motor vehicle under test, the storage container and the gas testing apparatus. Heat losses during the transfer of the gas from the motor vehicle to the storage container and from the storage container to the test apparatus as well as from the storage container itself can cause variations in the temperature and, thereby, the volume of gas and therefore a change in the percentage of the constituents of the gas leading to inaccurate test results.

Thus, it would be desirable to provide a gas emission sample container which maintains the temperature of gas stored therein at a constant temperature.

SUMMARY OF THE INVENTION

The present invention is a gas emission sample container including means for maintaining the temperature of gas stored within the container at a constant temperature.

The gas emission sample container is in the form of a sealed, expansible body having flexible side walls surrounding a hollow, sealed, expansible internal chamber or cavity. An aperture is formed in one of the flexible side walls and receives a fitting means which forms a gas flow path to the hollow cavity within the container. Temperature maintaining means are formed on the container for maintaining the temperature of gas stored within the container at a constant, predetermined temperature.

In one embodiment, the temperature maintaining means comprises heater means for generating heat and means for mounting the heater means on the container. The mounting means preferably comprises a receptacle formed externally on the container by a planar sheet attached to one of the side walls of the container. The sheet is attached to the one side wall along three side edges and forms a hollow receptacle between itself and the opposed side wall of the container which is accessible through an open end formed at one end of the sheet and the flexible side wall of the container. The heater means is removably mounted in the receptacle. The heater means preferably comprises an electric coil which is connectible to a source of electric power.

Optionally, reflective surface means are mounted in the receptacle adjacent the heater means for reflecting heat generated by the heater means toward the adjacent side wall of the container. Preferably, the side wall of the container immediately adjacent the heater means is formed of a black material to easily absorb heat from the heater means.

In a preferred construction of the container, one of the two sheets forming the container has a plurality of spaced projections formed thereon and extending from one surface of the sheet into the interior cavity within the container. Spaces are formed between adjacent projections on the one sheet and form gas flow paths over the entire surface of the one sheet to aid in the complete filling and evacuation of gas to and from the container. The opposed sheet of the container is formed of a black material for heat absorption purposes.

In another embodiment, the container is simply formed of one side wall having the aforementioned projections facing inward into the internal cavity of the container and an opposed side wall formed of an inert, black material. This embodiment is suited for use with an exterior heater means, such as an infrared heater, placed adjacent to the container. The black side wall of the container absorbs heat from the heater means to maintain the temperature of gas within the container at a constant, predetermined temperature during inflation, storage and subsequent evacuation of gas to and from the container.

The unique gas emission sample container of the present invention uniquely maintains the temperature of gas stored within the container at a constant predetermined temperature. This eliminates any variations in the volume of such stored gas caused by temperature variations as with previously devised gas emission storage containers. The temperature maintaining means is easily implemented on existing gas emission sample container constructions by means of forming an external receptacle for receiving a thin, planar heater means therein. Alternately, simply forming one side wall of the container of a black material provides heat absorption from an external heater to easily maintain the temperature of gas within the container at a constant predetermined temperature.

BRIEF DESCRIPTION OF THE DRAWING

The various features, advantages, and other uses of the present invention will become more apparent by referring to the following detailed description and drawing in which:

FIG. 1 is a plan view of a gas emission sample container;

FIG. 2 is a perspective view of the gas emission sample container shown in FIG. 1, taken from one major surface thereof, and showing a first embodiment of the present invention;

FIG. 3 is a cross sectional view generally taken along line 3—3 in FIG. 2; and

FIG. 4 is a side elevational view of a second embodiment of the gas emission sample container according to the present invention.

DESCRIPTION OF THE PREFERRED EMBODIMENTS

Referring now to the drawing, and to FIGS. 1-3 in particular, there is illustrated a gas emission sample container 10 which is connectible to a motor vehicle, for example, to collect and temporarily store gas emissions therefrom. The container 10 is also connectible to suitable test equipment, not shown, to supply such stored gas emissions to the test equipment for subsequent testing and/or analysis. As shown in FIGS. 1 and 2, the gas emission sample container 10 comprises a sealed enclosure of any shape, such as rectangular, square, circular, etc. It will be understood that a rectangular shape for the container 10 is illustrated by way of example only. Further, the container 10 may be provided in different sizes depending upon the requirements of a particular test application.

The sealed container or bag 10 is formed of two flexible sheets of chemically inert material. Preferably, fluorinated plastics chosen from the fluorocarbon family, such as those sold under the trademarks TEFLON, TEDLAR and HALAR, may be employed. As shown in FIG. 2, the sealed container 10 is formed of a first or front sheet 12 and a second or back sheet 14, each of a single thickness or ply. Typically, the single ply sheets 12 and 14 are 2 or 4 mils. in thickness. The front and back sheets 12 and 14, respectively, are sealingly connected at their peripheral edges by any suitable means, such as by the depicted heat seams 16. Such a sealing method forms a recess 18 on one side of the joined sheets 12 and 14 and a small projection or bump 20 on the opposite surface. For additional sealing capability, two spaced heat seams 16 may be employed about the peripheral edges of the front and back sheets 12 and 14. The seam or seams 16 seal the peripheral edges of the front and back sheets 12 and 14 and form a hollow, expandable, internal cavity 22, shown in FIG. 3, within the interior of the sealed container 10.

According to the present invention, at least one of the sheets, such as the first sheet 12 of the container 10, includes a plurality of spaced, discrete projections 24, as shown in FIG. 3. The projections 24 extend outward from one surface of the sheet 12 toward the opposed sheet 14 and are disposed in the interior cavity 22 of the sealed container 10. The projections 24 may have irregular shapes and may be disposed at irregular spacings as shown in FIG. 3. However, the projections 24 are preferably formed on substantially the entire surface of the sheet 12.

The projections 24 are formed in the sheet 14 by any suitable means, such as the use of rolls or a press which permanently deforms the sheet 14 into the desired projection shape and location. As shown in FIG. 3, the projections 24 generally taper from the surface of the sheet 14 to an apex. It will be understood that projections 24 having any other shape may also be employed to practice the present invention. Further details concerning the shape and construction of the projections 24 may be had by referring to pending and allowed U.S. patent application Ser. No. 07/905,900, the contents of which are incorporated herein by reference.

A plurality of gas flow paths are formed between the spaced, adjacent projections 24. The gas flow paths extend over substantially the entire surface of the sheet 14 and remain even when the container 10 is evacuated and the opposed sheet 14 is drawn into close registry or contact with the sheet 12. The gas flow paths thus insure a complete filling of the container 10 when gas is introduced into the interior cavity 22 of the container 10 through a fitting 30 as well as a complete evacuation of the entire volume of gas from the container 10 through the fitting 30.

The fitting 30 may have any conventional shape, such as that described in U.S. Pat. No. 5,074,155, the contents of which pertaining to the construction and use of the fitting are incorporated herein by reference.

The internal mixing fitting 30, as shown in FIG. 1, is mounted on the sealed container 10 for controlling the flow of gas to and from the interior 22 of the sealed container 10. The fitting 30 includes a body formed of a chemically inert material. Any suitable material, such as a fluorocarbon or fluorinated plastic may be employed. By way of example, fluorocarbons sold under the trademark TEFLON and those sold under trade or chemical names of TFE, PTFE, FEP, PFA and ECTFE, may be employed. Other fluorocarbonated plastics sold under the trademarks FLOUNS, HALARS and KYNAR may be employed. Additionally, polyvinylfluorines, sold under the trademark TEDLAR or trade names, PVF and PV2F, may also be employed.

The fitting 30 is provided with an external coupler 32 which is connectible to a suitable conduit, not shown, for supplying gas to the container 10 from a motor vehicle undergoing tests as well as to provide a gas flow path from the container 10 to suitable test equipment, also not shown, for evaluating the constituents of such gas emissions.

According to the present invention, the container 10 includes temperature maintaining means for maintaining the temperature of gas within the container 10 at a constant, predetermined temperature during such storage. In a first embodiment, shown in FIGS. 2 and 3, the temperature maintaining means includes a hollow receptacle 40 mounted externally on the container 10, adjacent one of the side walls, such as the side wall 14. The receptacle 40 is formed by sealingly attaching a planar sheet 42 to the side wall 14 of the container 10 along three side edges, thus leaving an open top end 44 allowing access to a hollow chamber 46 formed between the side wall 14 and the sheet 42. The planar sheet 42 may be attached to the side wall 14 of the container 10 by any suitable means. Preferably, heat seams 48, similar to the heat seams 16 described above, are formed along three side edges of the sheet 42 and through the side wall 14.

The planar sheet 42 may be formed of any suitable material, such as the fluorinated plastics, namely, TEFLON, TEDLAR, HALAR, described above for use in forming the side walls 12 and 14 of the container 10. Further, the sheet 42 is preferably black in color to provide heat absorption characteristics. However, it is not critical that the sheet 42 be black in color since the adjacent flexible side wall 14 of the container 10 is preferably formed of a black material to absorb heat from a heater means 50 mounted in the chamber 46.

The heater means 50 preferably comprises an electric coil wound in a plurality of turns arranged in a planar shape. The coil 52 is mounted between opposed surface layers 54 and 56. For example, the coil 52 may comprise a low watt heater manufactured by Watlow, model number H060100C1. This exemplary heater is a 120 volt, 300 watt heater and provides a low wattage of 1 to 2 watts per square inch over the entire surface of the heater 52.

A pair of leads 53 are connected to opposite ends of the coil 52 and are in turn connected to a source of electric power. Suitable sensors and/or temperature controllers, not shown, may be connected to the leads 53 to provide control of the heat generated by the heater means 52 and thereby the temperature of the gas within the container 10. If desired, temperature sensors may be mounted on the container 10 to sense the temperature of the gas stored therein. A temperature controller may be employed to control the activation of the heater means 52 to maintain the temperature of the gas at a selected, predetermined temperature.

Optionally, reflective surface means 56 are disposed adjacent to the exterior surface of the heater means 50 within the chamber 46. Preferably, the reflective surface means 56 is formed of aluminum or stainless steel, by example, to reflect heat generated by the heater means 50 away from the reflective surface 56 and toward the side wall 14 of the container 10.

In use, the heater means 50 is simply inserted into the chamber 46 formed between the planar sheet 42 and the flexible side wall 14 of the container 10. The leads 53 are then connected to a source of electric power which causes the heater means 50 to generate heat. Such heat is absorbed by the preferable black construction of the flexible side wall 14 and transferred to the gas within the container 10, after such gas has been supplied to the container 10.

FIG. 4 depicts a second embodiment of the present invention. In this embodiment, the container 60 is formed substantially identical to the container 10 described above and shown in FIG. 1. The container 60 includes opposed flexible side walls 12 and 14 which are sealingly joined together at their peripheral edges by heat seams 16. A fitting 30 is mounted on the side wall 12 and communicates with the hollow interior cavity formed within the container 60 between the side walls 12 and 14.

The side wall 14 is preferably formed of a black material, such as black TEFLON, TEDLAR or HALAR. The container 60 lacks the heater receptacle 40 shown in FIGS. 2 and 3. In this embodiment, the temperature maintaining means comprises an external heater 62, such as an infrared heater, which is located adjacent to and in proximity with the container 60, such as adjacent one edge of the container 60 as shown in FIG. 4. Heat from the heater 62 is absorbed by the black side wall 14 and conducted to the gas stored within the container 60 to maintain the temperature of the gas 60 at a predetermined temperature. Suitable sensors and a temperature controller, not shown, may be employed to maintain the temperature of the gas within the container 60 at a predetermined temperature by controlling the timed activation and deactivation of the heater 62 as needed.

In summary, there has been disclosed a unique gas emission storage container which includes novel means for maintaining the temperature of gas stored within the container at a constant, predetermined temperature. In one embodiment, the heater means is uniquely mounted on the container adjacent one of the side walls thereof. This requires no modification to the existing gas emission sample container except for the mounting of a planar sheet to form a receptacle on the container for receiving the heater therein. In another embodiment, one of the side walls of the container is formed of a black material to provide enhanced heat absorption from an external heater located adjacent to the container.

What is claimed is:

1. A stand alone gas emission sample container for receiving, storing and discharging a constant volume of gas emissions, the container comprising:

a sealed, expansible member having flexible side walls surrounding a hollow, expansible internal cavity;

fitting means, mounted in one of the side walls of the container, for forming a closable gas flow path to the interior cavity therein; and heating means for maintaining the temperature of gas stored in the container at a predetermined temperature; and means for mounting the heating means on the expansible member.

2. A stand alone gas emission sample container for receiving, storing and discharging a constant volume of gas emissions, the container comprising:

a sealed, expansible member having flexible side walls surrounding a hollow, expansible internal cavity;

fitting means, mounted in one of the side walls of the container, for forming a closable gas flow path to the interior cavity therein; and temperature maintaining means for maintaining the temperature of gas stored in the container at a predetermined temperature, the temperature maintaining means including heater for generating heat and a receptacle formed exteriorly on the container adjacent one of the side walls thereof, the heater means being mountable in the receptacle.

3. The container of claim 2 wherein the receptacle comprises:

a sheet attached to one of the side walls of the container and forming an open ended receptacle in conjunction with the one side wall.

4. The container of claim 2 wherein:

the heater means is removably mounted in the receptacle.

5. The container of claim 2 wherein the heater means comprises:

an electric coil connectible to a source of electric power.

6. The container of claim 5 wherein:

the electric coil is wound in a plurality of turns arranged in a common plane.

7. The container of claim 2 further comprising:

reflective surface means, mounted in the receptacle, for reflecting heat generated by the heater means toward the adjacent side wall of the container.

8. The container of claim 2 wherein the temperature maintaining means further comprises:

the side wall of the container adjacent the receptacle being formed of a dark material to absorb heat from the heater means.

9. The container of claim 8 wherein:

the container is formed of first and second flexible sheets sealingly joined together at their peripheral edges;

the one of the first and second sheets of the container adjacent to the receptacle being formed of a dark material.

* * * * *